(12) United States Patent
Bencic et al.

(10) Patent No.: US 10,073,023 B2
(45) Date of Patent: Sep. 11, 2018

(54) LIGHT EXTINCTION TOMOGRAPHY FOR MEASUREMENT OF ICE CRYSTALS AND OTHER SMALL PARTICLES

(71) Applicants: Timothy J. Bencic, Highland Heights, OH (US); David P. Rohler, Shaker Heights, OH (US); Amy F. Fagan, Fairview Park, OH (US); Steven H. Izen, Shaker Heights, OH (US); Arjun K. Maniyedath, Beachwood, OH (US)

(72) Inventors: Timothy J. Bencic, Highland Heights, OH (US); David P. Rohler, Shaker Heights, OH (US); Amy F. Fagan, Fairview Park, OH (US); Steven H. Izen, Shaker Heights, OH (US); Arjun K. Maniyedath, Beachwood, OH (US)

(73) Assignee: Plexar Associates, Inc., Shaker Heights, OH (US)

( * ) Notice: Subject to any disclaimer, the term of this patent is extended or adjusted under 35 U.S.C. 154(b) by 149 days.

(21) Appl. No.: 15/170,715

(22) Filed: Jun. 1, 2016

(65) Prior Publication Data
US 2016/0274017 A1  Sep. 22, 2016

Related U.S. Application Data

(63) Continuation-in-part of application No. 14/751,085, filed on Jun. 25, 2015.

(60) Provisional application No. 62/017,143, filed on Jun. 25, 2014.

(51) Int. Cl.
*G01N 21/00* (2006.01)
*G01N 15/06* (2006.01)
*G01N 33/00* (2006.01)
*G01N 15/00* (2006.01)
*G01N 33/18* (2006.01)

(52) U.S. Cl.
CPC ......... *G01N 15/06* (2013.01); *G01N 33/0009* (2013.01); *G01N 33/0031* (2013.01); *G01N 33/0036* (2013.01); *G01N 2015/0026* (2013.01); *G01N 2015/0046* (2013.01); *G01N 2015/0693* (2013.01); *G01N 2033/1873* (2013.01)

(58) Field of Classification Search
CPC ........... G01N 15/06; G01N 2015/0026; G01N 2015/0046; G01N 2015/0693; G01N 2033/1873; G01N 33/0009; G01N 33/0031; G01N 33/0036; G01N 21/53; G01N 33/004; G01N 15/1463; G01N 1/2252; G01N 2291/021; G01N 2291/0215; G01N 2291/02845
USPC ........................................... 356/337
See application file for complete search history.

(56) References Cited

U.S. PATENT DOCUMENTS

| 4,950,073 A * | 8/1990 | Sommer | B82Y 15/00 356/37 |
| 7,173,257 B1 * | 2/2007 | Warrick | G01N 15/0255 250/458.1 |
| 2017/0001137 A1 * | 1/2017 | Lans | B01D 46/0086 |

\* cited by examiner

*Primary Examiner* — Sunghee Y Gray
(74) *Attorney, Agent, or Firm* — Ulmer & Berne LLP (57) ABSTRACT

A tomography duct for wind tunnels includes a plurality of light sources and sensors displaced around a support structure. The light sources are cycled and sensor measurements are made from sensors opposite the light sources. Tomographic algorithms are used to determine an extinction map from the sensor measurements. The extinction map provides details about particles in a cross-section of the air flow through the tomography duct.

10 Claims, 8 Drawing Sheets

FIG. 9

LIGHT EXTINCTION TOMOGRAPHY FOR MEASUREMENT OF ICE CRYSTALS AND OTHER SMALL PARTICLES

CROSS-REFERENCE TO RELATED APPLICATIONS

This application is a continuation-in-part of application Ser. No. 14/751,085 filed Jun. 25, 2015, which claims the benefit of U.S. Provisional No. 62/017,143, filed Jun. 25, 2014, each of which is herein incorporated by reference in its entirety.

STATEMENT REGARDING FEDERALLY SPONSORED RESEARCH OR DEVELOPMENT

This invention was made with government support under contract #NNC112CA25C awarded by NASA/Glenn Research Center. The government has certain rights in the invention.

STATEMENT REGARDING PRIOR DISCLOSURES BY AN INVENTOR OR JOINT INVENTOR

This subject matter of the present disclosure was presented to the American Institute of Aeronautics and Astronautics on Jun. 25, 2013, in AAIA Paper No. 2013-2678, authored by Bencic, T J, Fagan, A F, Van Zante, J F, Kirkegaard, J P, Rohler, D P, Maniyedath, A, and Izen, S H, and titled "Advanced Optical Diagnostics for Ice Crystal Cloud Measurements in the NASA Glenn Propulsion Systems Laboratory."

TECHNICAL FIELD

The subject application teaches embodiments that relate generally to a system of optical emitters and detectors configured to detect particle density in a cross section flow between the emitters and detectors, and specifically to an optical tomography system configured to detect ice or water particle density in a cross section of a flow through a wind tunnel.

SUMMARY

In an example embodiment, a system includes a support frame, a first number of electromagnetic emitters, a second number of electromagnetic detectors, and a controller. The support frame surrounds partly or fully surrounds a cavity through with a flow of air can pass without being interfered with substantially. The electromagnetic emitters are displaced along the support frame and are configured to emit electromagnetic radiation toward the cavity and illuminated at least a cross-section of the flow of air. The electromagnetic detectors are also displaced along the support frame, for example interleaved with the electromagnetic emitters. The electromagnetic detectors care configured to detect the electromagnetic radiation emitted from the electromagnetic emitters. The controller is configured to cycle on-and-off each of the plurality of electromagnetic emitters in an illumination pattern. During each on cycle, the controller acquires a measurement from a selected group of electromagnetic detectors, for example those electromagnetic detectors situated approximately opposite the electromagnetic emitter that is cycled on. From the acquired measurements, the controller reconstructs an extinction map of the cross-section of the flow of air using a tomography algorithm. The controller determines characteristics of the particles in the flow of air from the reconstructed extinction map. The electromagnetic emitter can be an optical light emitter, monochromatic, spectrally filtered, an LED, a laser, or a light source coupled to a fiber optic waveguides such as a fiber optic cable. The electromagnetic detector can be a pixel of a CCD or charge coupled device, one or more pixels of a CCD, or a fiber optic waveguide coupled to a portion of a CCD. The system can include a fiber coupler configured to couple fiber optic waveguides such as fiber optic cables to a CCD sensor. The system can include collection widening optics for the emitters or detectors. They support frame can substantially surround the cavity. The support frame in conjunction with parts of the emitters and detectors can form a tomography duct that is displaced in a wind tunnel between a sprayer and an engine under test. The wind tunnel generates the flow of air and the sprayer injects particles of water, supercooled water, or ice into the flow of air. The tomography algorithm can include algorithms such as an iterative reconstruction algorithm, a filtered backprojection algorithm, a truncated singular value decomposition algorithm, and diffraction tomographic reconstruction In an example embodiment, a method includes measuring dark current of a sensor element before the light source illuminates the tomography duct through which an air flow can be passed, and then emitting light from a light source across the tomography duct to a sensor element position across the tomography duct. On the sensor element, the impinging unextinguished light intensity can be measured and the tomography algorithm can be calibrated based on the dark current and measure of the unextinguished light intensity. A plurality of particles can be received into the air flow and the sensor element then measures an extinguished light intensity based on the plurality of particles in the air flow. The calibrated tomography algorithm reconstructs an extinction map of a cross-section of the air flow based on the extinguished light intensity. The method can also include generating the air flow and injecting the plurality of particles into the air flow, which can be water droplets, supercooled water droplets, or ice particles. The method can include adjusting the intensity of light emitted from the light source based on the measured unextinguished light intensity. The method can include determining characteristics of the particles in the air flow based on the reconstructed extinction map.

In an example embodiment, a method includes positioning a geometric simulation component in a tomography duct of a wind tunnel, illuminating light sources displaced in tomography duct in an illumination pattern, and receiving light that is partially extinguished by one or more features of the geometric simulation component by one or several sensor displaced in the tomography duct. The method includes measuring the extinguished light intensity from selected sensor elements during each of the illumination cycles in the illumination pattern, and based on measurements, reconstructing an extinction map using a tomography algorithm. The method includes comparing the reconstructed extinction map with an expected extinction map correlated with the geometric simulation component, and adjusting the parameters of the tomography algorithm based on the comparison. The method can perform the adjusting in an iterative fashion by repeating some or all of the above steps. The geometric simulation component can be cross-shaped to test radial resolution of the tomography duct or ring-shaped to test angular resolution, and can include multiple concentric rings.

BACKGROUND

There have been over 200 documented cases of jet engine power loss events during flight at high altitudes due to ingestion of ice particles. The events typically occur at altitudes above 22,000 feet and near deep convective systems, often in tropical regions. It is recognized in the industry that supercooled liquid water does not exist in large quantities at these high altitudes and therefore it is expected that the events are due to the ingestion of ice particles.

Based on this recent interest in ice particle threat to engines in flight, the NASA Glenn Research Center (GRC) installed the capability to produce ice crystal and mixed phase water clouds in the Propulsion Systems Laboratory (PSL) Test Cell 3. The ice crystal cloud operational parameters, developed with input from industry, were Median Volumetric Diameter (MVD) from 40 to 60 pm and Total Water Content (TWC) from 0.5 to 9.0 g/m3. The PSL is currently the only engine test facility that can simulate both altitude effects and an ice crystal cloud. It is a continuous flow facility that creates the temperature and pressure inlet conditions that propulsion systems experience in high-speed, high-altitude flight. Specifically for the icing system, the total temperature can be controlled between +45 to −60 F, pressure altitude from 4,000 to 40,000 feet (facility limit is 90,000 feet), and Mach from 0.15 to 0.8 (facility limit is Mach 3.0).

Within this facility, there was a specific need to develop a non-intrusive system to measure the conditions of a cloud that enters an aircraft engine in the PSL. The system should (1) have the capability to be operated remotely, (2) have minimal optical access, (3) no moving parts, (4) fast acquisition and (5) good resolution in a pipe that can structurally support an aircraft engine in close proximity. An earlier study of this problem is described in "Application of the Radon Transform to Calibration of the NASA-Glenn Icing Research Wind Tunnel," by Izen, S H, and Bencic, T J, in Contemporary Mathematics, Vol. 278, 2001, pp. 147-166.

DETAILED DESCRIPTION

The systems and methods disclosed herein are described in detail by way of examples and with reference to the figures. It will be appreciated that modifications to disclosed and described examples, arrangements, configurations, components, elements, apparatuses, devices methods, systems, etc. can suitably be made and may be desired for a specific application. In this disclosure, any identification of specific techniques, arrangements, etc. are either related to a specific example presented or are merely a general description of such a technique, arrangement, etc. Identifications of specific details or examples are not intended to be, and should not be, construed as mandatory or limiting unless specifically designated as such.

The systems and methods disclosed herein describe a light extinction tomography system for use in detecting small liquid and solid (ice) water particles in various spray conditions. Visible light laser diodes are pulsed across an area of interest and the extinction or loss of light intensity is measured at many different directions. The attenuated light projections across the field of view can be reconstructed to yield an image of the particles that crossed the plane of light. This is analogous to Computed Tomography (CT) in the medical imaging field in which slices of density through the body can generate images in the interior. Although the disclosed system and method are described below with regard to visible light and water particles, the system and method also can be used with any suitable electromagnetic emitters and detectors, and any suitable solid, fluid, or gas as would be understood in the art.

The optical tomography system and method determines particle density detection. An example application considered here is the measurement of ice or ater particle density in a cross section of a flow through a wind tunnel, though other applications of the disclosure are also contemplated, for example as detailed below.

Figure 1:
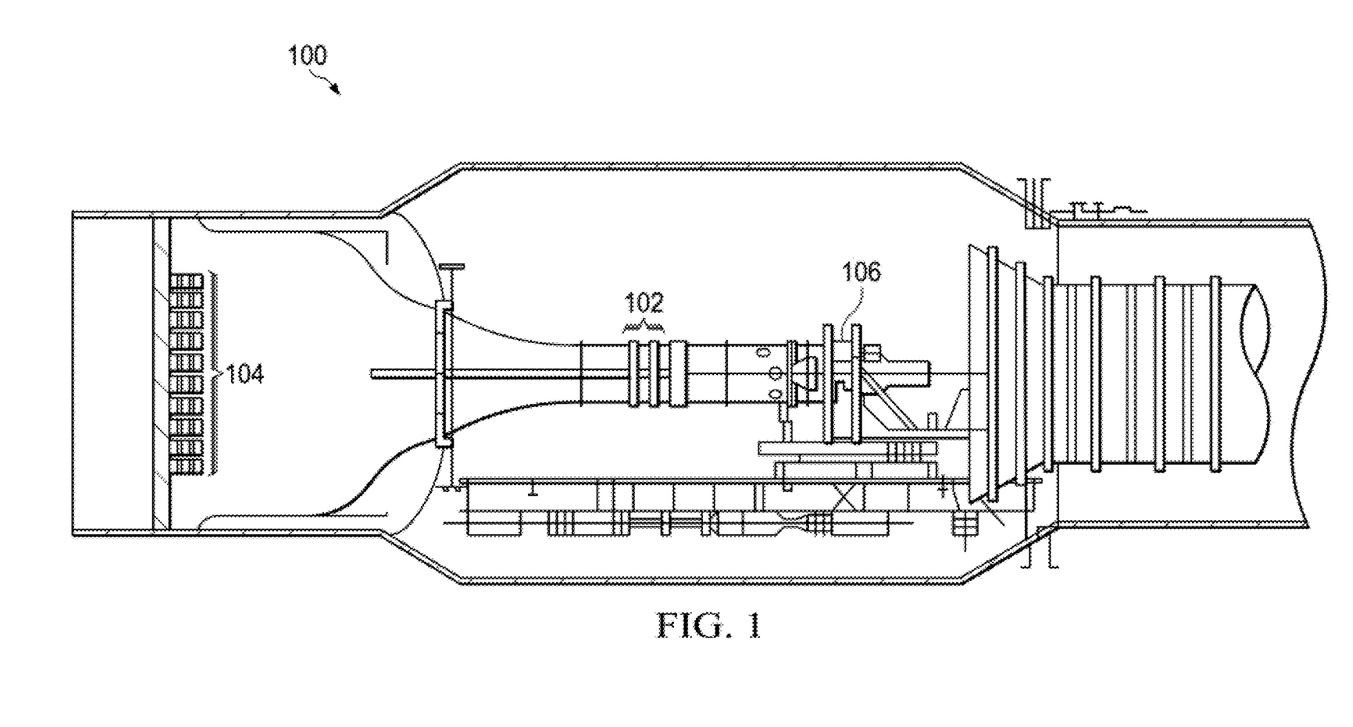
FIG. 1 is a schematic drawing of a wind tunnel depicting the location of a tomography duct relative to spray bars and an engine to be tested according to an embodiment of the disclosure.

Turning to FIG. 1, in an embodiment a tomography duct 102 is integrated into the walls 108 of a wind tunnel 100 so as not to impede or otherwise interfere with the air flow being measured. The tomography duct 102 generally surrounds an internal space, or cavity, through which the air flows. In the wind tunnel, a sprayer such as spraybars 104 inject particles into the air flow directed into an engine 106 that is under test.

Figure 2:
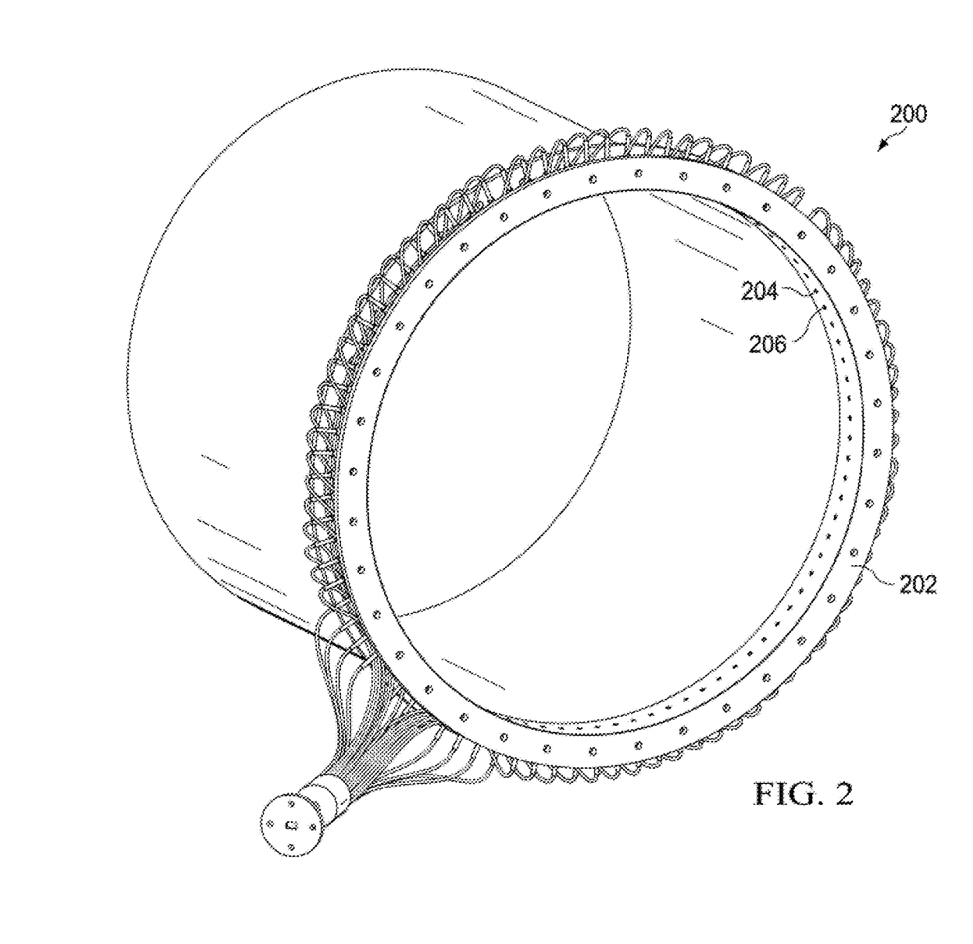
FIG. 2 is a first view of a representation of a light extinction tomography system installed in the NASA/Glenn Propulsion Systems Lab (PSL) at the tomography duct pipe exit according to an embodiment of the disclosure.
Figure 3:
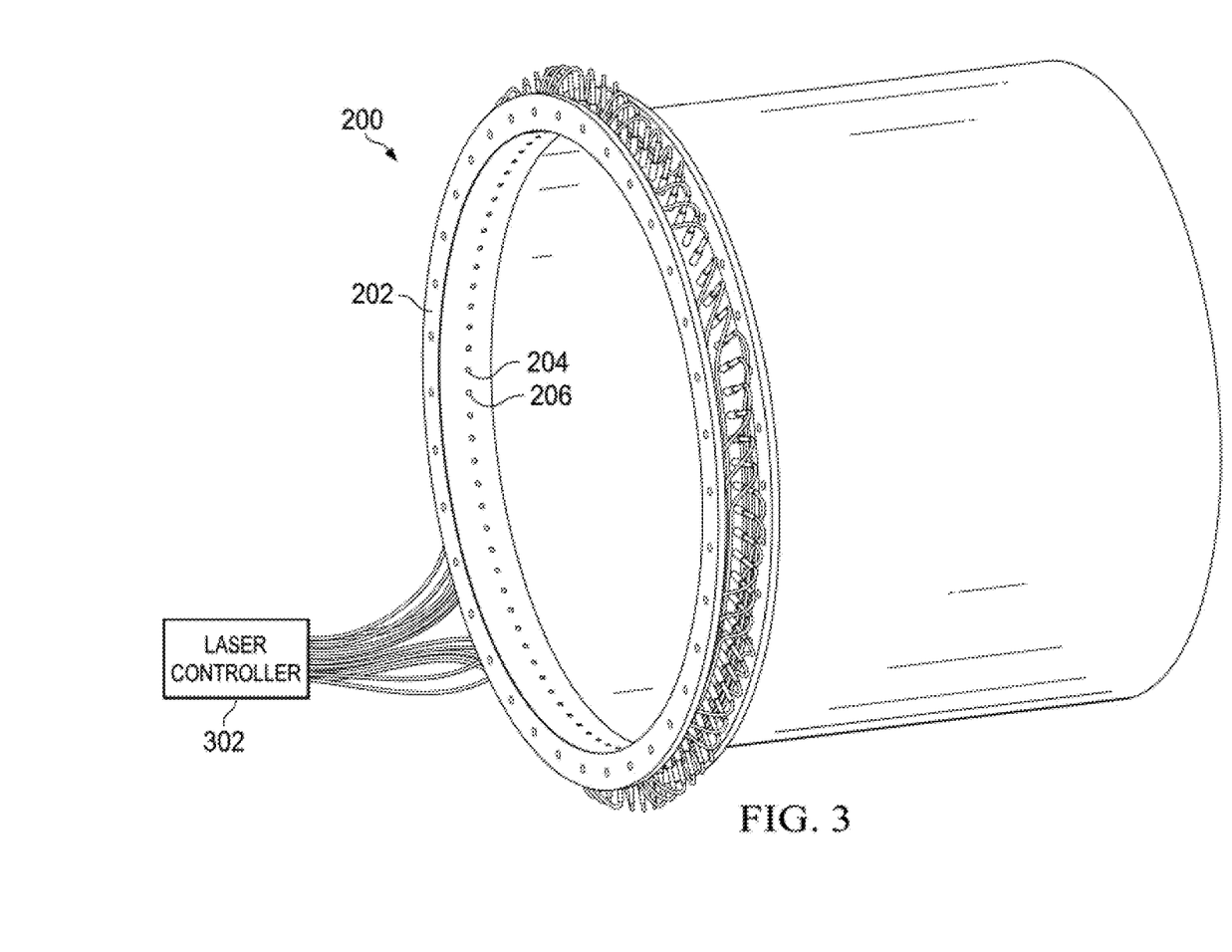
FIG. 3 is a second view of the light extinction tomography system of FIG. 2 illustrating cabling, laser sources, and optical detectors according to an embodiment of the disclosure.

Turning now to FIGS. 2 and 3, in an embodiment a tomography duct 200 includes a support frame 202, a set of light sources 204 that are distributed around the support frame 202, and a set of optical detectors 206 that are distributed around the support frame 202. The optical tomography system also includes a control system (not shown) configured to illuminate the light sources 204 in a desired illumination pattern, a detections system (not shown) configured to collect measurements from the optical detectors 206, a processing system (not shown) to reconstruct an extinction map from the measurements on the optical detectors 206. The control system (not shown) can be further configured to provide a user interface and coordinate the illumination and measurement functions.

The support frame 202 is nominally circular to conform to the wall of the wind tunnel in which the frame is to be mounted. In some embodiments the support frame 202 becomes part of the wall of the wind tunnel. In other embodiments, the support frame 202 can be inserted into the wind tunnel and mounted within the wind tunnel. The system of the subject disclosure can be configured to work in any size wind tunnel provided the support frame 202 is suitably scaled to the size of the wind tunnel. The support frame can be made of metal or other advanced structural materials, as would be understood in the art. The light sources 204 and optical detectors can be mounted onto the support frame 202. For example, the light sources 204 and optical detectors 206, along with any optics, can be flush mounted so as not to interfere with the flow being measured.

Figure 4:
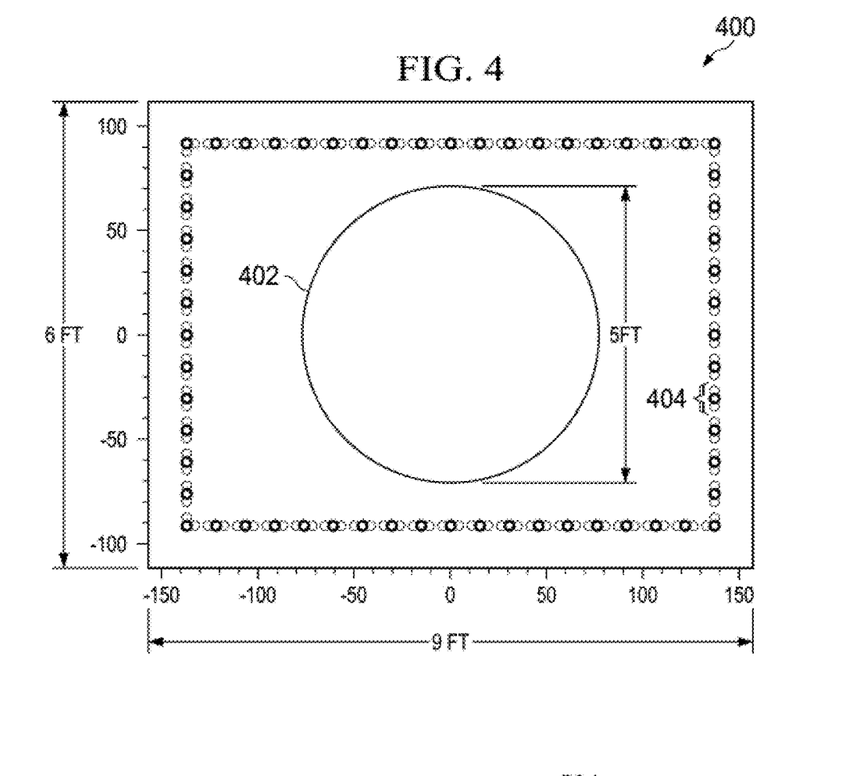
FIG. 4 is a schematic illustration of a rectangular icing research tunnel.

Referring also to FIG. 4, in other embodiments a support frame 400 can have a non-circular cross-section. For example, if the system of the subject disclosure were to be used in the NiSA-Glenn Icing Research Tunnel, the support frame would have a rectangular cross-section similar to the support frame 400 shown in FIG. 4. The inner circle 402 designates the region for which accurate imaging is desired and the small dots 404 represent candidate positions of light sources and optical detectors according to an embodiment of the disclosure.

Refer now to the light sources 204 of FIGS. 2, 3, and 4. Because the purpose of the system is to reconstruct particle density by measuring optical extinction, bright light sources 204 are distributed around the support frame 202. The extinction along rays from each light source 204 is measured on one or multiple optical detectors 206. In an embodiment, the light sources 204 are lasers, the illumination of which can be precisely controlled by electrical signals. For example, as shown in FIG. 3, a laser controller 302 can pulse the laser light sources 204 in accordance with an illumination pattern. Although lasers are used in this embodiment, other intense light sources 204 could also be used as would be understood in the art, including but not limited to light emitting diodes. In an embodiment, one or more light sources 204 can be placed in the controller 302 and coupled to the support frame 202 via an optical waveguide such as a fiber optic cable. It can be desirable for the extinction model to use monochromatic light. In an embodiment the lights sources 204 emit monochromatic light. In an embodiment spectral filters can also be used with the light sources 204 to produce monochromatic light. As would be understood in the art, the system can use any suitable frequency or frequencies of electromagnetic radiation, including but not limited to the optical light, infrared light, ultraviolet light, and so forth. Therefore the light sources 204 can be configured to emit electromagnetic radiation of one or more desired frequencies while the optical detectors 206 can be configured to detect electromagnetic radiation of one or more desired frequencies.

In the present embodiment, it is desired to reconstruct particle density along a plane roughly transverse to the flow through the wind tunnel. Accordingly, it is desirable to focus the energy along an illumination half-plane. For example, this can be accomplished with collimation, such as is described in U.S. Pat. No. 6,184,989, filed Apr. 26, 1999 and titled "Laser sheet tomography apparatus for flow field statistics". In the present disclosure, the subject system provides an improved solution through the use of optical elements configured to focus the light energy onto a half plane and disperse the energy as evenly as possible among all directions from the source into the half-plane. In embodiments, due to practical construction requirements, it can be necessary to shift the sources slightly off the plane of reconstruction. This configuration will have the effect of reducing illumination onto detectors located close to the source. This configuration should not have a major impact on reconstructed particle density.

The optical detectors 206 are sensors mounted along the support frame 202 which are sensitive to light. The optical detectors 206 measure the optical extinction along each path from the light sources 204 to the optical detectors 206. In a configuration, the optical detectors 206 have wide collection angles, and can include optics surrounding each optical detector 206 to widen the collection angle. While in an embodiment the optical detectors 206 on the support frame 202 can be fiber optic cables with collection angle widening optics, other detection options will also work. For example suitable fiber optic waveguides, including fiber optic cables, splitters, and so forth can be used, or individual detectors can be used. In an embodiment, each end of the fiber optic cables opposite that collecting the light from the light sources 204 is mounted so as to point directly at a known location on a charge-coupled device (CCD) array. Thus, the light intensity on the optical detector 206 can be measured by a CCD readout. As a practical consideration, the system of the present disclosure may have extra fibers not normally attached to the support frame 202 which can be used as spares to replace defective optical detectors 206 attached to the support frame 202.

The optical detectors 206 are nominally distributed on the support frame 202 in the plane of illumination. The optical detectors 206 may be slightly off the desired plane of reconstruction if practical mounting constraints require it. In an embodiment, on a circular frame the optical detectors 206 are evenly spaced and either completely or partially interlaced with the light sources 204. The positions of the light sources 204 and optical detectors 206, together, determine the "geometry" of the acquisition. In various embodiments, other geometries can include features such as non-uniform spacing between either the light sources 204, optical detectors 206, or both. In embodiments, the geometries include light sources 204 and/or optical detectors 206 that are slightly displaced from the measurement plane. In embodiments, the geometries include evenly spaced optical detectors 206 shifted by a fixed amount from the nominal interlaced geometry. One such embodiment is known as a quarter detector shift. In an embodiment, optical detectors 206 can be placed outside of the direct source illumination plane in order to make measurements of scatter.

The measurement model has some similarity to that arising in medical Computed Tomography (CT). However, our application has several significant differences. In both medical applications and ours, the sources are in a ring outside the object and detectors are situated on a fan across from the source. However, in medical applications, the object of interest occupies a relatively small region about the center of the source ring. In the present application, the detectors are situated on the source ring, and the region of interest encompasses the entire interior of the cross-section, (though the central region here is also of primary importance).

The particle density distribution is computed by measuring the optical extinction along rays from the sources to the detectors. This data is reconstructed using tomographic algorithms to give a probability of extinction at a given location in the cross section. Using extinction models with expected particle size distributions, the material density can be recovered. In the present embodiment, the extinction model uses single particle scattering. If in other applications, a single particle scattering model is not sufficient, diffraction tomographic reconstruction techniques can be used instead of the Radon inversion methods used with the single scattering model.

To measure optical extinction with the preferred embodiment, three steps are needed. First, the acquisition CCD is calibrated by measuring the dark current. That is, with no sources illuminated, data are acquired. This gives a measure of the detection signal in the absence of stimulation, and allows the actual measurements to be calibrated. Typically, this does not need to be repeated frequently, as it is a characteristic of the measurement CCD camera.

Next, data are acquired with no flow or particles present. This gives the unextinguished light intensities. Finally, measurements are taken in the presence of particles. The ratio of the Log of intensities (after the dark current is subtracted) gives the extinction along the optical paths from each source to each detector. These extinction data along with the source and detector "geometry" are input to the tomographic reconstruction algorithms. Specifically, the model can include detector response characteristics related to (1) the incident angle of the source-detector line relative to the detector surface and (2) the source-detector distance.

While performing the flow absent measurement, various experimental anomalies can be detected. For example, defective sources and/or detectors can be identified. Also, detector gain levels can be calibrated to avoid saturation, or maximize signal-to-noise ratios. Relative sensitivity profiles can be determined and exploited in reconstruction algorithms. Modifications to reconstruction algorithms to handle missing or unreliable data from known source-detector pairs can be incorporated. Anomalies (such as a part from the test section protruding into the measurement plane) during the flow-present acquisition can also be detected and handled.

Figure 5:
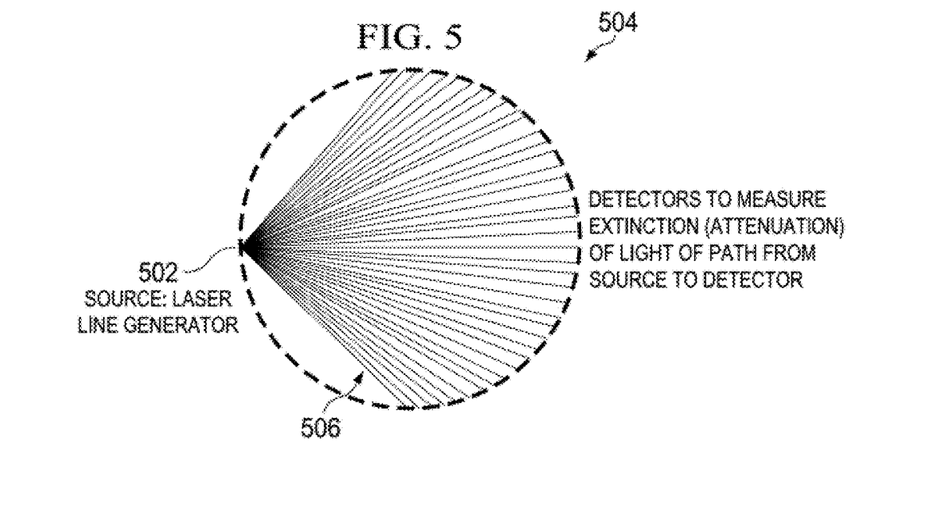
FIG. 5 is a schematic illustration of the optical path for one laser source and the detectors that receive useful signals from that source according to an embodiment of the disclosure.

Refer also to FIG. 5. In order to perform an acquisition, the control circuitry pulses one source 502 at a time and can be performed under computer control. With the one source 502 active, each detector 504 measures the light intensity from that source along the connecting ray 506. In the preferred embodiment, this light is conducted to a specific region on a CCD in a high precision CCD camera. The charge on the CCD sensor is read using the camera capabilities. The readout time from the CCD is the limiting factor in the timing of the source pulses. In an embodiment, by custom design of camera readout protocols, the readout can be restricted only to the regions of the CCD onto which fibers have been connected. This significantly reduces readout time, advantageously enabling a higher repetition rate.

The source pulse-readout sequence is repeated for each source on the support frame. After every source has been pulsed, sufficient data is available for the reconstruction engine to generate a particle density profile. The order in which each source is pulsed is referred to as the source pattern. Example patterns can be simply pulsing adjacent sources sequentially, or pulsing in a "star illumination pattern" and then sequentially using adjacent stars until all sources have been pulsed. For example, in an embodiment with 60 sources numbered sequentially from 1 to 60, one five point star would be sources 1, 25, 49, 13, 37. So the "star" illumination pattern would be 1, 25, 49, 13, 37, 2, 26, 50, 14, 38, 3, 27, 51, 15, 39, and so forth. Other source patterns can be used as would be understood by one of ordinary skill in the art.

The star illumination patterns can be more robust with respect to time variations in the flow during acquisition. The illumination pattern to be used can be selected by the user and supported by the controlling hardware and software.

Tomographic reconstruction can be the recovery of a quantity from a collection of line integrals of the quantity or from a collection of integrals of the quantity over a narrow strip. The relevant quantity for this application is liquid water content. For the particle sizes expected in our embodiment and the optical path lengths across the measurement section, the extinction of a beam of light passing through the spray will be proportional to the line integral or strip integral of liquid water content along the optical path.

For a single scattering model, the measurements can be converted to samples of the Radon transform of the extinction probability per unit length. In the present embodiment, novel methods, with some similarity to those used in commercial CT scanners, are used to recover the profile of the extinction probability per unit length (and hence the particle density). However, other methods specific to this application can also be used. For example, basis functions incorporating only low spatial frequencies can be used instead of the pixel based basis functions, as the expected particle densities do not have profiles with sharp edges for which high spatial frequencies are needed. Also, missing data can be handled by projection completion or interpolation. Alternatively, iterative reconstruction algorithms can also be applied. Note that some such algorithms which are not feasible in a medical setting are applicable here due to the reduced size of the data set.

Because the reconstruction region extends to the source ring, the standard reconstruction algorithms used in a medical setting must be modified to avoid significant artifacts. Another difference is that our sample density is much lower, so the available resolution in the reconstruction of the spray will be relatively low. On the other hand, since the spray itself is not expected to have sharp transitions, this is not expected to be a problem. Moreover, this a priori information can be exploited by modeling the spray as a superposition of low spatial frequency functions, such as Gaussian shaped blobs.

In addition, as a consequence of the implementations for some of the reconstruction methods discussed above, a method can be employed to provide almost real-time temporal updates. After data for a full image has been obtained, each time a source has been pulsed as part of the next acquisition, the data from that partial acquisition can replace the data from the previous pulsing of the same source. Only the new data needs to be processed to obtain an updated image. This idea can be applied to data obtained from any group of sources, such as a star in the star illumination patterns.

As an alternative to the traditional medical-type reconstruction, an algorithm has been developed which incorporates this a priori knowledge to reduce the computational complexity. It should be noted that the alternative algorithm does not scale well to the medical setting, but is well suited for use with the sampling densities available here. In this algorithm, the measurements are simulated for each possible Gaussian blob. The acquired spray measurement is fit to a linear combination of the simulated blob measurements. The corresponding linear combination of low spatial frequency functions is taken as the reconstructed image. This method is easily adapted to handle minor malfunctions in the acquisition system such as a dark source, or a dead detector.

In order to reduce streaking artifacts, the sampled data can be up-sampled from 120×60 to 480×240. This up-sampling preserves the original bandwidth of the data. The reconstruction is based on this original bandwidth and does not improve the resolution, even though the reconstruction is performed on a finer grid. Although this method does well in the central ⅔ of the field of view, it is not as robust in the outer ring due to the uneven coverage of source-detector paths through the outer ring, and also because the filtered backprojection algorithm relies on an approximation which is less valid at reconstruction points close to the source ring.

For the rectangular frame as shown in FIG. 4, a different reconstruction method can be successfully used. The Truncated Singular Value Decomposition (TSVD) algorithm is a well-known method for regularizing the solution for the matrix equation, y=Rx.

In the context of the rectangular geometry, the column vector y holds the measured data, with each element corresponding to a source-detector pair. Each element of the column vector x corresponds to the cloud density at a position within the rectangular geometry. The matrix R represents the integrals over each source detector pair which takes a cloud distribution x to the measurement y.

Because the linear equation is typically both over or under constrained, it is solved by use of the pseudo-inverse, $R^+$. The solution vector $x=R^+ y$, is the vector x with minimum norm that also minimizes the size of the residual y-Rx.

Unfortunately, when $R^+$ is ill-conditioned, meaning that some components in the data y will have a greatly magnified influence in the solution x, it is necessary to regularize R+ as noise in the measurements (random, system, or numerical) will be amplified in the solution, swamping the reconstruction. Regularization effectively removes this inordinate amplification. The TSVD algorithm limits the acceptable magnification by ignoring the components in the data which would be unduly amplified in the solution. There is a trade-off between reconstruction resolution and fidelity and noise amplification which is tuneable by selection of a noise amplification threshold.

The application of the TSVD algorithm involves a time consuming computation of the SVD (singular value decomposition) of the matrix R. This computation grows like the 4th power of the number of linear pixels in the reconstructed image. Fortunately, the SVD only needs to be computed once (offline), so it will not significantly impact cloud reconstructions.

Raw data and reconstructed density patterns can be archived. The subject system can include a module for analysis of reconstructed density patterns. In particular, temporal averaging of density patterns is available (and also available in real time).

Referring now also to FIGS. 6A, 6B, 6C, and 6D, the subject system can include a simulator that has two (2) key capabilities. (1) Phantom object data can be generated according to specified parameters. (2) Measurement data can be produced using a phantom object and a model of the measurement system.

Figure 6A:
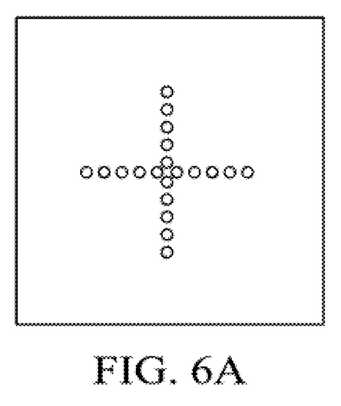
FIG. 6A is an illustration of an ideal cross image.
Figure 6B:
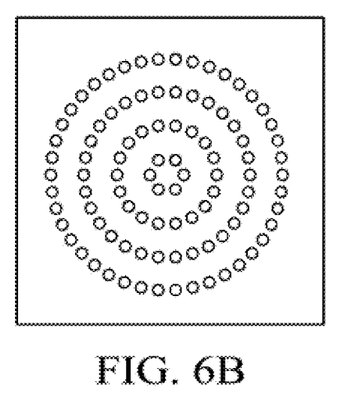
FIG. 6B is an illustration of an ideal circles image.
Figure 6C:
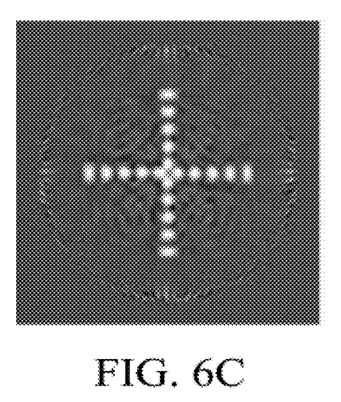
FIG. 6C is an illustration of a cross image reconstructed by a reconstruction algorithm according to an embodiment of the disclosure.
Figure 6D:
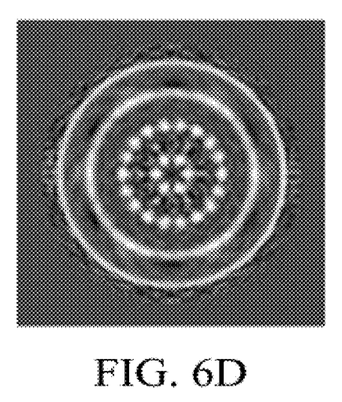
FIG. 6D is an illustration of a circles image reconstructed by a reconstruction algorithm according to an embodiment of the disclosure.

The phantom object can include cloud components or geometric components. Cloud components are used, for example, to characterize the fidelity provided by the measurement system and the reconstruction. Geometric components are used, for example, to characterize the spatial resolution of the measurement system and the reconstruction. In FIGS. 6A and 6B, geometric simulation components are shown. In FIG. 6A, a cross-shaped geometric simulation component uses pins that are placed 2-inches apart, thus there is a 1-inch gap between each pin. The pins can be hollow as shown or solid. In FIG. 6B, a circles-shaped geometric simulation component uses rings of pins where each ring is places so that the circumferential gap is 1-inch between the 1-inch pins. The cross-shaped geometric simulation component tests radial resolution and the circles-shaped geometric simulation component will test angular resolution. FIG. 6C shows the result of reconstructing the cross-shaped geometric simulation component and FIG. 6D shows the result of reconstructing the circles-shaped geometric simulation component using one embodiment of the reconstruction algorithm.

By specifying various parameters of the measurement system, the simulator can be used to determine an effective hardware design. The simulator advantageously aids in the design of the reconstruction algorithm and parameters.

Figures 7A, 7B, 7C:
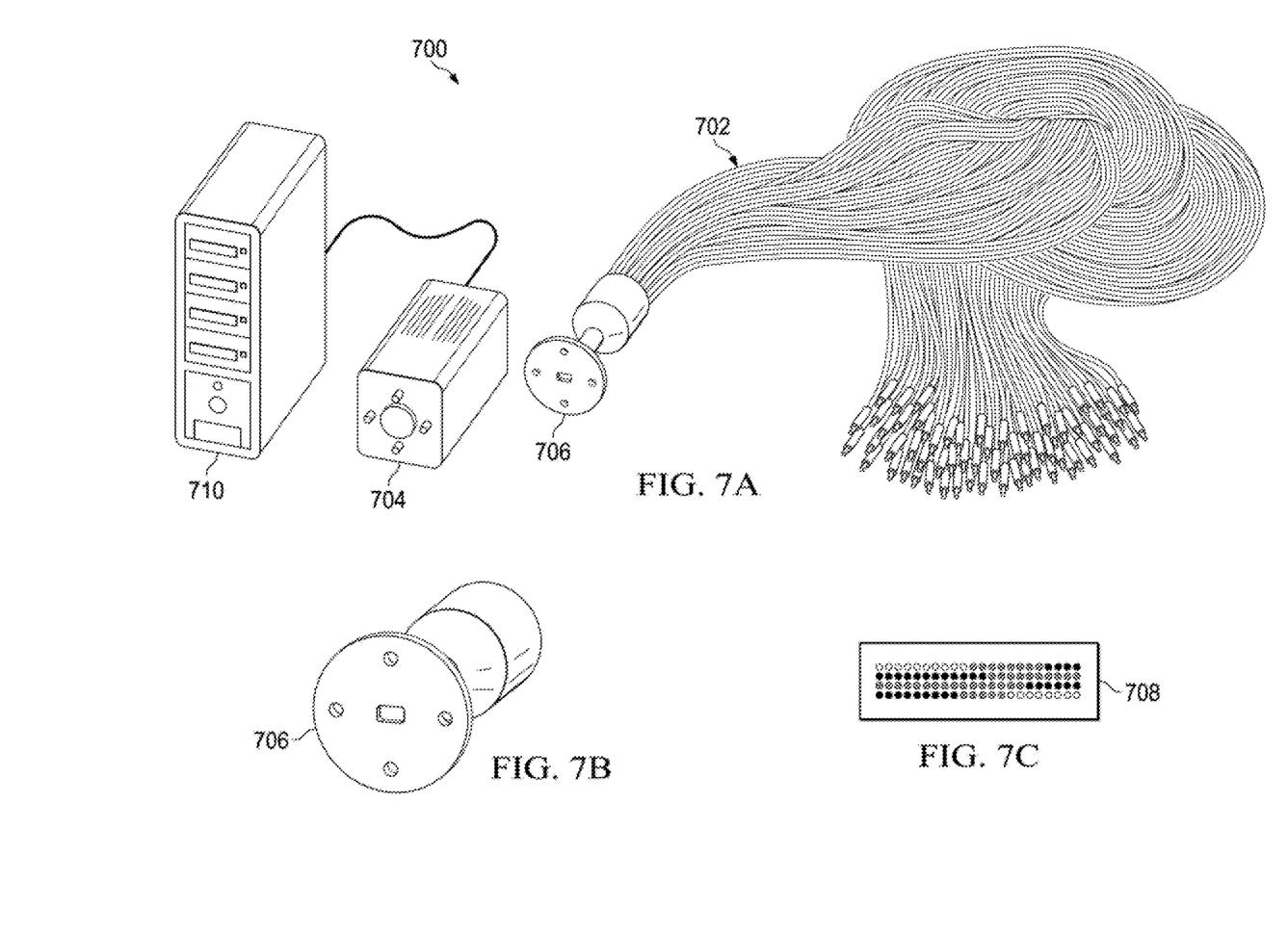
FIG. 7A is an illustration of a detection system that includes a fiber coupling, associated optical fibers, and a camera element according to an embodiment of the disclosure.
FIG. 7B is an illustration of a fiber coupling for communicating light to a camera element according to an embodiment of the disclosure.
FIG. 7C is an illustration of a sample data image of light collected by 120 fibers of the detection system of FIG. 7A.

Referring back to FIGS. 2, and 3, an embodiment of a light extinction tomography system consists of 60 equally spaced laser diodes with sheet generating optics and diffusing elements providing >300 degree coverage around the ring and 120 fiber optically coupled detection elements mounted every 3 degrees around a 36-inch diameter ring. Each detector utilizes a flashed opal input diffuser at the fiber entrance which is coupled to the CCD camera for simultaneous sampling of all 120 channels. The diffuser allows coupling of the laser light into the fibers at a very wide input angle of approximately +/−85 degrees with respect to the fiber face. The diffusers greatly increase the acceptance angle of the fibers at the cost of allowing only a small amount of the incident light to be coupled into the fiber. The laser diode sources are pulsed sequentially while the detectors acquire line-of-sight extinction data for each laser pulse. A custom timing/triggering circuit was built in-house and used to control the data acquisition. Referring now also to FIGS. 7A, 7B, and 7C, optical fibers and a detection system are illustrated. The optical fibers 702 are direct coupled to the CCD 704 through a fiber optic faceplate 706, or fiber coupling. The imaged fibers are read out as a 5×5 pixel binned region of interest 708 in the center of the fiber which yields a pixel per fiber or a 120 pixel image per sequential laser scan. A controller 710 is in data communication with the CCD 704 and receives the image. In an embodiment, the timing/trigger circuit can be combined with the controller 710. In various embodiments, the controller 710 can perform any suitable operation described above, including but not limited to the executing the tomography algorithms. In other embodiments, individual controllers can separately perform different operations.

Using the computed tomography algorithms discussed in the previous section the extinction data is used to produce a plot of the relative water content in the measurement plane with spatial resolution better than 1 inch over the central 75% of the measurement area.

Figure 8A:
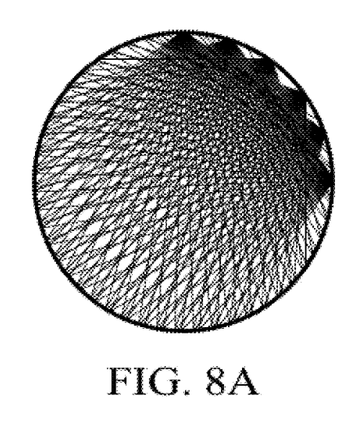
FIG. 8A is an illustration of the coverage provided by the projections of multiple light sources to detectors according to an embodiment of the disclosure.

Referring now to FIG. 8A, lines from several sources and the corresponding projections to the detectors are illustrated.

Figure 8B:
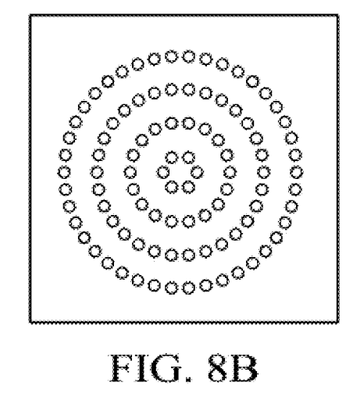
FIG. 8B is an illustration of a phantom image for use in demonstrating resolution quality differences between the center ring and the outer regions near the wall of the ring according to an embodiment of the disclosure.
Figure 8C:
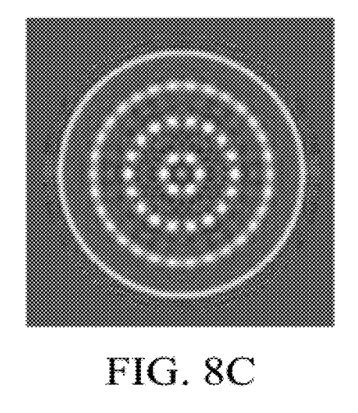
FIG. 8C is an illustration of resolution quality provided by the detection system according to an embodiment of the disclosure.

This gives some indication about the expected resolution as the area near the wall has a minimal amount of line crossing in multiple directions. Referring now to FIG. 8B, a resolution study was performed to determine the expected resolution across the duct plane using simulated phantom data of 1 inch circles. Referring now to FIG. 8C, a reconstruction was performed of the simulated line projection information. The reconstruction of the 60 source, 120 detector configuration is shown in FIG. 8C illustrates the loss of resolution with increasing radial distance from the center of the duct. The 1 inch circles are clearly evident in the inner two rings which represent approximately a 12 inch diameter. The third ring of circles from the center are now turned into ovals which shows a loss of angular resolution but each dot can still be recognized, this corresponds to a diameter of approximately 20 inches. The outermost dots are completely blended together at approximately a 30 inch diameter. This study was performed using a high spatial frequency model because of the abrupt high contrast of the dots on the black background. This high spatial resolution leads to reconstruction artifacts which can be ignored since the intent of the study is to confirm the expected resolution and not to minimize the reconstruction noise.

The subject system and method can be used as a particle density detection system for a number of suitable applications, including but not limited to the following. In an embodiment, the system and method can be used to measure the density of ice or water particles inside a wind tunnel in real time and provide an archival record of particle density. In particular, spray patterns can be visualized. Anomalies in spray patterns, such as inoperative or malfunctioning nozzles or spray hot spots, can be detected. The system and method can be used for engineering desired sprays and spray patterns.

In an embodiment, the system and method can be used as part of a wind tunnel instrumentation, for example to provide feedback and control for spray settings, both automatic or manually with human intervention.

Figure 9:
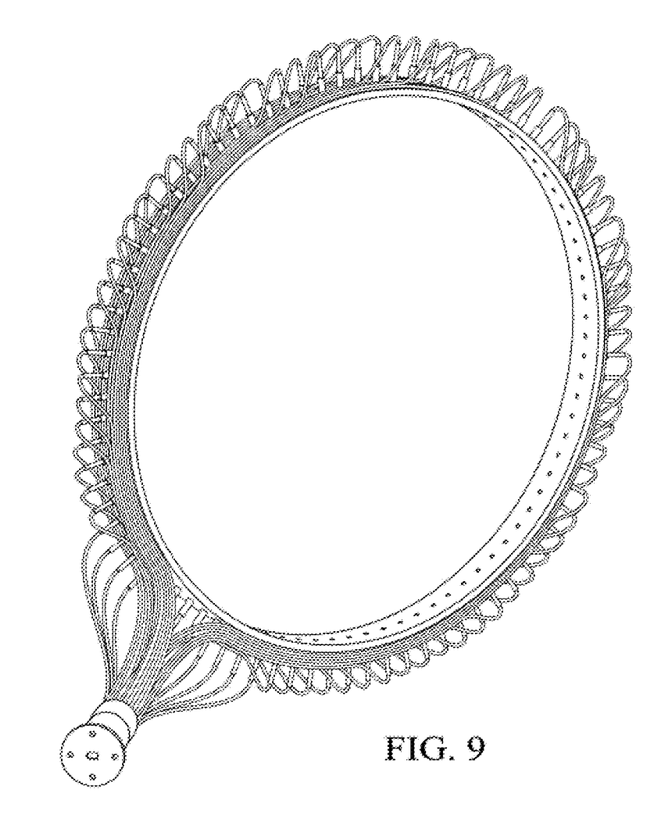
FIG. 9 is an illustration of a tomography ring for measuring the density of a water spray according to an embodiment of the disclosure.

In an embodiment, the system and method can provide measurement of a general spray system such as paint or water, for example in an industrial setting as illustrated in FIG. 9, which also possibly can include a control element.

In an embodiment, the system can be mounting in the intake of a jet engine to provide real time and archival records of flight conditions. Upon detection of dangerous icing conditions, a system could alert the pilot and/or adjust engine parameters to ensure safe operation.

In an embodiment, the system and method can be used to measure atmospheric particulate density, for example volcanic ash or from other sources of emissions.

In an embodiment, the system and method can be used to compare historical data for repeatability and to determine trends for sources, detectors and sprays, including individual nozzles.

In an embodiment, the system and method can be used for analyzing smoke stack emissions. The frequencies used for the electromagnetic emitters can be configured to absorption peaks of the effluents or particles being detected.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the spirit and scope of the inventions.

What is claimed is:

1. A system, comprising:
   a support frame at least partially surrounding a cavity through which a flow of air can pass without substantial interference;
   a plurality of electromagnetic emitters displaced along the support frame and configured to emit electromagnetic radiation toward the cavity to illuminate at least a cross-section of the flow of air;
   a plurality of electromagnetic detectors displaced along the support frame and configured to detect the electromagnetic radiation emitted from the electromagnetic emitters; and
   a controller configured to
      cycle on-and-off each of the plurality of electromagnetic emitters in an illumination pattern,
      acquire a measurement from each of one or more selected electromagnetic detectors during each on-cycle of an electromagnetic emitter,
      reconstruct, from a plurality of acquired measurements, an extinction map of the cross-section of the flow of air using a tomography algorithm, and
      determine one or more characteristics of particles in the flow of air from the reconstructed extinction map.

2. The system of claim 1, wherein the electromagnetic emitters and the electromagnetic detectors are displaced along the support structure in an interleaved configuration.

3. The system of claim 1, wherein each electromagnetic emitter is selected from the group consisting of an optical light emitter, a monochromatic light generating emitter, a light emitter coupled with a spectral filter to emit monochromatic light, a light emitting diode, a laser, and a light emitter coupled to a fiber optic waveguide.

4. The system of claim 1, wherein each electromagnetic detector is selected from the group consisting of a pixel of a charge coupled device, one or more pixels of a charge coupled device, and a fiber optic waveguide coupled to at least a portion of a charge coupled device.

5. The system of claim 1, further comprising:
   a fiber coupler, associated with the electromagnetic emitters, configured to couple a plurality of fiber optic waveguides to a charge coupled device sensor.

6. The system of claim 1, further comprising:
   a plurality of collection widening optics in communication with one or more of the electromagnetic emitters or electromagnetic detectors.

7. The system of claim 1, wherein the support frame substantially surrounds the cavity.

8. The system of claim 1, further comprising:
   a wind tunnel configured to generate the flow of air;
   a sprayer configured to inject particles into the flow of air;
   an engine mount for positioning an engine under test in the wind tunnel; and
   a tomography duct displaced in the wind tunnel between the sprayer and the engine mount, the tomography duct comprising the support frame and at least a portion of the electromagnetic emitters and the electromagnetic detectors.

9. The system of claim 1, wherein the particles are selected from the group consisting of water, supercooled water, and ice.

10. The system of claim 1, wherein the tomography algorithm includes an algorithm selected from the group consisting of an iterative reconstruction algorithm, a filtered backprojection algorithm, a truncated singular value decomposition algorithm, and diffraction tomographic reconstruction.

\* \* \* \* \*